United States Patent
Kraus et al.

(10) Patent No.: US 9,309,572 B2
(45) Date of Patent: Apr. 12, 2016

(54) ACID CERAMIDASE POLYMORPHISMS AND METHODS OF PREDICTING TRAITS USING THE ACID CERAMIDASE POLYMORPHISMS

(75) Inventors: William E. Kraus, Durham, NC (US);
Lauren R. Simel, Durham, NC (US);
Mark P. Donahue, Durham, NC (US);
Elizabeth R. Hauser, Durham, NC (US)

(73) Assignee: Duke University, Durham, NC (US)

( * ) Notice: Subject to any disclaimer, the term of this patent is extended or adjusted under 35 U.S.C. 154(b) by 714 days.

(21) Appl. No.: 13/318,768

(22) PCT Filed: May 3, 2010

(86) PCT No.: PCT/US2010/033410
§ 371 (c)(1),
(2), (4) Date: Nov. 3, 2011

(87) PCT Pub. No.: WO2010/129477
PCT Pub. Date: Nov. 11, 2010

(65) Prior Publication Data
US 2012/0065080 A1    Mar. 15, 2012

Related U.S. Application Data

(60) Provisional application No. 61/175,186, filed on May 4, 2009.

(51) Int. Cl.
*C12P 21/06* (2006.01)
*C12Q 1/68* (2006.01)

(52) U.S. Cl.
CPC ........ *C12Q 1/6876* (2013.01); *C12Q 2600/124* (2013.01); *C12Q 2600/156* (2013.01)

(58) Field of Classification Search
None
See application file for complete search history.

(56) References Cited

U.S. PATENT DOCUMENTS

2005/0272054 A1    12/2005    Cargill et al.
2008/0070247 A1    3/2008    Ruano et al.

OTHER PUBLICATIONS

NCBI Reference Sequence: NM_004315.4.
Adams JM II, Pratipanawatr T, et. al. "Ceramide content is increased in skeletal muscle from obese insulin-resistant humans" Diabetes 53: 25-31, 2004.
Barrett, J.C., Fry, B., Maller, J. &Daly, M.J. "Haploview: analysis and visualization of LD and haplotype maps" Bioinformatics 21,263-265 (2005).

(Continued)

*Primary Examiner* — Reza Ghaforian
(74) *Attorney, Agent, or Firm* — Michael Best & Friedrich LLP

(57) ABSTRACT

Provided are methods of predicting a trait in a subject including obtaining information about at least a portion of a polynucleotide sequence of the subject, the polynucleotide sequence encoding the acid ceramidase polypeptide, and using the information to predict the expression of the trait in the subject. Further provided are methods of developing a treatment plan for a subject with a disease or condition responsive to exercise. The methods may include obtaining information about at least a portion of a polynucleotide sequence of the subject, the polynucleotide sequence encoding the acid ceramidase polypeptide, using the information to predict a trait selected from maintaining an exercise program and physiological responsiveness to an exercise program, and developing a treatment plan for the subject to treat the disease or condition.

9 Claims, 4 Drawing Sheets

LD White

LD Black

(56) References Cited

OTHER PUBLICATIONS

Birbes H, EI Bawab S, et. al. "Mitochondria and ceramide: intertwined roles in regulation of apoptosis" Advan. Enzyme Regul. 2002 (42): 113-129.

Blachnio-Zabielska A, Baranowski M, et.al. Effect of exercise duration on the key pathways of ceramide metabolism in rat skeletal muscles. J. Cell. Biochem. 2008 (105): 776-784.

Boros et al., "Elucidation of the ELK1 target gene network reveals a role in the coordinate regulation of core components of the gene regulation machinery" Genome Res. Published online Aug. 17, 2009, pp. 1-11.

Bray MS, Hagberg JM, et. al. "The Human Gene Map for Performance and Health-Related Fitness Phenotypes: The 2006-2007 Update" Med. Sci. Sports Exerc. 2009 (41): 34-72.

Bruce CR, Thrush AB, et. al. "Endurance training in obese humans improves glucose tolerance and mitochondrial fatty acid oxidation and alters muscle lipid content" Am J Physiol Endocrinol Metab 291: E99-E107, 2006.

Chavez JA, Holland WL, et. al. "Acid ceramidase overexpression prevents the inhibitory effects of saturated fatty acids on insulin signaling" The Journal of Biological Chemistry 2005 (280): 20148-20153.

Dobrzyn A, Gorski J. "Ceramides and sphingomyelins in skeletal muscles of the rat: content and composition. Effect of prolonged exercise" Am J Physiol Endocrinol Metab 2002 (281): E277-E285.

Ingelsson E, Larson MG, et. al. "Heritability, Linkage, and Genetic Associations of Exercise Treadmill Test Responses" Circulation 2007 (115): 2917-2924.

Feitosa MF, Rice T, et. al. "Evidence of QTLs on chromosomes 13q and 14q for triglycerides before and after 20 weeks of exercise training: The HERITAGE Family Study" Atherosclerosis 2007 (182): 349-360.

Flegal K, Carroll M, et. al. "Overweight and Obesity in the United States: prevalence and trends" 1960-1994. Int J Obes Relat Metab Disord 1998 (22): 39-47.

Gudz TI, Tserng K, et.al. "Direct inhibition of mitochondrial respiratory chain complex III by cellpermeable ceramide" J Biol Chem 1997 (272): 24154-24158.

Hannun YA, Obeid LM. "The ceramide-centric universe of lipid-mediated cell regulation: stress encouters of the lipid kind" The Journal of Biological Chemistry 2002 (277): 25847-25850.

Haskell WL, Lee I, et. al. "Physical activity and public health: Updated recommendation for adults from the American College of Sports Medicine and the American Heart Association" Circulation 2007 (116): 1081-1093).

Helge JW, Dobrzyn A, et. al. "Exercise and training effects on ceramide metabolism in human skeletal muscle" Exp Physio/2004 (89): 119-127.

Kraus WE, et. al. "Studies of targeted risk reduction intervention through defined exercise (STRRIDE)" Medicine and Science in Sports and Exercise 2001 (33): 1774-1784.

Mao C, Obeid LM. "Ceramidases: regulators of cellular responses mediated by ceramide, sphingosine, and sphingosine-1-phosphate" Biochimica et Biophysica Acta 2008 (1781): 424-434.

Di Paola M, Cocco T, et. al. "Ceramide interaction with respiratory chain of heart mitochondria" Biochemistry 2000 (39): 6660-6668.

Park J, Schuchman EH. "Acid ceramidase and human disease" Biochimica et Biophysica Acta 2006 (1758): 2133-2138.

Park TS, Panek RL, et al "Inhibition of sphingomyelin synthesis reduces atherogenesis in apoplipoprotein E-knockout mice" Circulation 2004 (110) 3465-3471.

Ruano G, Seip RL, et. al. "Apolipoprotein Al genotype affects the change in high density lipoprotein cholesterol subfractions with exercise training" Atherosclerosis 2006 (185): 65-69.

Samad F, Hester KD, et. al. "Altered adipose and plasma sphingolipid metabolism in obesity: a potential mechanism for cardiovascular and metabolic risk" Diabetes 2006 (55): 2579-2587.

Summers SA. "Ceramides in insulin resistance and lipotoxicity" Progress in Lipid Research 2006 (45): 42-72.

Teran-Garcia M, Santora N, et. al. "Hepatic lipase gene variant -514C>T is associated with lipoprotein and insulin sensitivity response to regular exercise: The HERITAGE Family Study" Diabetes 2005 (54): 2251-2255.

Unger RH, Zhou Y. "Regulation of fatty acid homeostasis in cells: Novel role of leptin" PNAS 1999 (96): 2327-2332.

Wang Y, Beydoun MA, et. al. Will all Americans become overweight or obese? Estimating the progression and cost of the US obesity epidemic Obesity 2008 (16): 2323-2330.

Xu H, Gregory SG, et. al. "SNPselector: a web tool for selecting SNPs for genetic association studies" Bioinformatics 2005 (21): 4181-4186.

Zhou Y, Grayburn P, et. al. Lipotoxic heart disease in obese rats: implications for human obesity. PNAS 2000 (97): 1784-1789.

Simel, Genetic Variation in Acid Ceramidase Predicts Failure to Complete an Exercise Intervention. Aug. 7, 2009, Abstract (Retrieved on Jul. 15, 2010).

NCBI Refernce Sequence: NM_004315.4.

PCT/US2010/033410 International Preliminary Report on Patentability and Written Opinion dated Nov. 17, 2011 (9 pages).

PCT/US2010/033410 International Search Report dated Aug. 11, 2010 (3 pages).

SEQUENCE LISTING

```
<160> NUMBER OF SEQ ID NOS: 5

<210> SEQ ID NO 1
<211> LENGTH: 2551
<212> TYPE: DNA
<213> ORGANISM: Homo sapiens

<400> SEQUENCE: 1
agtgcaaccc agagggcagg atttcctgct ggactttgaa atccaacccg gtcacctacc      60
cgcgcgactg tgtccacgga tggcacgaaa gccaagcgag tccccctgcc gagctactcg     120
cgtccgcctc ctcccaagct gagctctgct ccgcccacct gagtccttcg ccagttagga     180
ggaaacacag ccgcttaatg aactgctgca tcgggctggg agagaaagct cgcgggtccc     240
accgggcctc ctacccaagt ctcagcgcgc ttttcaccga ggcctcaatt ctgggatttg     300
gcagctttgc tgtgaaagcc caatggacag aggactgcag aaaatcaacc tatcctcctt     360
caggaccaac gtacagaggt gcagttccat ggtacaccat aaatcttgac ttaccaccct     420
acaaaagatg gcatgaattg atgcttgaca aggcaccagt gctaaaggtt atagtgaatt     480
ctctgaagaa tatgataaat acattcgtgc caagtggaaa aattatgcag gtggtggatg     540
aaaaattgcc tggcctactt ggcaactttc ctggcccttt tgaagaggaa atgaagggta     600
ttgccgctgt tactgatata cctttaggag agattatttc attcaatatt ttttatgaat     660
tatttaccat ttgtacttca atagtagcag aagacaaaaa aggtcatcta atacatggga     720
gaaacatgga ttttggagta tttcttgggt ggaacataaa taatgatacc tgggtcataa     780
ctgagcaact aaaaccttta acagtgaatt tggatttcca aagaaacaac aaaactgtct     840
tcaaggcttc aagctttgct ggctatgtgg gcatgttaac aggattcaaa ccaggactgt     900
tcagtcttac actgaatgaa cgtttcagta taaatggtgg ttatctgggt attctagaat     960
ggattctggg aaagaaagat gtcatgtgga tagggttcct cactagaaca gttctggaaa    1020
atagcacaag ttatgaagaa gccaagaatt tattgaccaa gaccaagata ttggccccag    1080
cctactttat cctgggaggc aaccagtctg gggaaggttg tgtgattaca cgagacagaa    1140
aggaatcatt ggatgtatat gaactcgatg ctaagcaggg tagatggtat gtggtacaaa    1200
caaattatga ccgttggaaa catcccttct tccttgatga tcgcagaacg cctgcaaaga    1260
tgtgtctgaa ccgcaccagc caagagaata tctcatttga aaccatgtat gatgtcctgt    1320
caacaaaacc tgtcctcaac aagctgaccg tatacacaac cttgatagat gttaccaaag    1380
gtcaattcga aacttacctg cgggactgcc ctgacccttg tataggttgg tgagcacacg    1440
tctggcctac agaatgcggc ctctgagaca tgaagacacc atctccatgt gaccgaacac    1500
tgcagctgtc tgaccttcca aagactaaga ctcgcggcag gttctctttg agtcaatagc    1560
ttgtcttcgt ccatctgttg acaaatgaca gatctttttt ttttcccct atcagttgat    1620 ttttcttatt tacagataac ttcttaggg gaagtaaaac agtcatctag aattcactga    1680
gttttgtttc actttgacat ttggggatct ggtgggcagt cgaaccatgg tgaactccac    1740
ctccgtggaa taaatggaga ttcagcgtgg gtgttgaatc cagcacgtct gtgtgagtaa    1800
cgggacagta aacactccac attcttcagt ttttcacttc tacctacata tttgtatgtt    1860
```

-continued

```
tttctgtata acagccttt ccttctggtt ctaactgctg ttaaaattaa tatatcatta   1920
tctttgctgt tattgacagc gatataattt tattacatat gattagaggg atgagacaga   1980
cattcacctg tatatttctt ttaatgggca caaaatgggc ccttgcctct aaatagcact   2040
ttttggggtt caagaagtaa tcagtatgca aagcaatctt ttatacaata attgaagtgt   2100
tccctttttc ataattactc tacttcccag taaccctaag gaagttgcta acttaaaaaa   2160
ctgcatccca cgttctgtta atttagtaaa taaacaagtc aaagacttgt ggaaaatagg   2220
aagtgaaccc atattttaaa ttctcataag tagcattcat gtaataaaca ggttttagt    2280
ttgttcttca gattgatagg gagttttaaa gaaattttag tagttactaa aattatgtta   2340
ctgtatttt cagaaatcaa actgcttatg aaaagtacta atagaacttg ttaacctttc    2400
taaccttcac gattaactgt gaaatgtacg tcatttgtgc aagaccgttt gtccacttca   2460
ttttgtataa tcacagttgt gttcctgaca ctcaataaac agtcactgga aagagtgcca   2520
gtcagcagtc atgcacgctg attgggtgtg t                                  2551
```

<210> SEQ ID NO 2
<211> LENGTH: 411
<212> TYPE: PRT
<213> ORGANISM: Homo sapiens

<400> SEQUENCE: 2

```
Met Asn Cys Cys Ile Gly Leu Gly Glu Lys Ala Arg Gly Ser His Arg
1               5                   10                  15

Ala Ser Tyr Pro Ser Leu Ser Ala Leu Phe Thr Glu Ala Ser Ile Leu
            20                  25                  30

Gly Phe Gly Ser Phe Ala Val Lys Ala Gln Trp Thr Glu Asp Cys Arg
        35                  40                  45

Lys Ser Thr Tyr Pro Pro Ser Gly Pro Thr Tyr Arg Gly Ala Val Pro
    50                  55                  60

Trp Tyr Thr Ile Asn Leu Asp Leu Pro Pro Tyr Lys Arg Trp His Glu
65                  70                  75                  80

Leu Met Leu Asp Lys Ala Pro Val Leu Lys Val Ile Val Asn Ser Leu
                85                  90                  95

Lys Asn Met Ile Asn Thr Phe Val Pro Ser Gly Lys Ile Met Gln Val
            100                 105                 110

Val Asp Glu Lys Leu Pro Gly Leu Leu Gly Asn Phe Pro Gly Pro Phe
        115                 120                 125

Glu Glu Glu Met Lys Gly Ile Ala Ala Val Thr Asp Ile Pro Leu Gly
    130                 135                 140

Glu Ile Ile Ser Phe Asn Ile Phe Tyr Glu Leu Phe Thr Ile Cys Thr
145                 150                 155                 160

Ser Ile Val Ala Glu Asp Lys Lys Gly His Leu Ile His Gly Arg Asn
                165                 170                 175

Met Asp Phe Gly Val Phe Leu Gly Trp Asn Ile Asn Asn Asp Thr Trp
            180                 185                 190

Val Ile Thr Glu Gln Leu Lys Pro Leu Thr Val Asn Leu Asp Phe Gln
        195                 200                 205

Arg Asn Asn Lys Thr Val Phe Lys Ala Ser Ser Phe Ala Gly Tyr Val
    210                 215                 220

Gly Met Leu Thr Gly Phe Lys Pro Gly Leu Phe Ser Leu Thr Leu Asn
225                 230                 235                 240

Glu Arg Phe Ser Ile Asn Gly Gly Tyr Leu Gly Ile Leu Glu Trp Ile
```

-continued

```
                        245                 250                 255
Leu Gly Lys Lys Asp Val Met Trp Ile Gly Phe Leu Thr Arg Thr Val
            260                 265                 270

Leu Glu Asn Ser Thr Ser Tyr Glu Glu Ala Lys Asn Leu Leu Thr Lys
        275                 280                 285

Thr Lys Ile Leu Ala Pro Ala Tyr Phe Ile Leu Gly Gly Asn Gln Ser
    290                 295                 300

Gly Glu Gly Cys Val Ile Thr Arg Asp Arg Lys Glu Ser Leu Asp Val
305                 310                 315                 320

Tyr Glu Leu Asp Ala Lys Gln Gly Arg Trp Tyr Val Val Gln Thr Asn
            325                 330                 335

Tyr Asp Arg Trp Lys His Pro Phe Phe Leu Asp Asp Arg Arg Thr Pro
            340                 345                 350

Ala Lys Met Cys Leu Asn Arg Thr Ser Gln Glu Asn Ile Ser Phe Glu
            355                 360                 365

Thr Met Tyr Asp Val Leu Ser Thr Lys Pro Val Leu Asn Lys Leu Thr
            370                 375                 380

Val Tyr Thr Thr Leu Ile Asp Val Thr Lys Gly Gln Phe Glu Thr Tyr
385                 390                 395                 400

Leu Arg Asp Cys Pro Asp Pro Cys Ile Gly Trp
            405                 410
```

<210> SEQ ID NO 3
<211> LENGTH: 51
<212> TYPE: DNA
<213> ORGANISM: Artificial Sequence
<220> FEATURE:
<223> OTHER INFORMATION: Synthetic

<400> SEQUENCE: 3
gtcatgtaag agtaagattg tgaccrttta gtcatattta ataacccact t       51

<210> SEQ ID NO 4
<211> LENGTH: 51
<212> TYPE: DNA
<213> ORGANISM: Artificial Sequence
<220> FEATURE:
<223> OTHER INFORMATION: Synthetic

<400> SEQUENCE: 4
tgactgctga ctggcactct ttccartgac tgtttattga gtgtcaggaa c       51

<210> SEQ ID NO 5
<211> LENGTH: 51
<212> TYPE: DNA
<213> ORGANISM: Artificial sequence
<220> FEATURE:
<223> OTHER INFORMATION: Synthetic

<400> SEQUENCE: 5
ctattagtac ttttcataag cagttkgatt tctgaaaaat acagtaacat a       51

ACID CERAMIDASE POLYMORPHISMS AND METHODS OF PREDICTING TRAITS USING THE ACID CERAMIDASE POLYMORPHISMS

CROSS-REFERENCE TO RELATED APPLICATIONS

This application is a national stage filing under 35 U.S.C. 371 of, and claims the benefit of priority to, International Patent Application No. PCT/US2010/033410, filed May 3, 2010, which claims the benefit of priority to U.S. Provisional Application No. 61/175,186, filed May 4, 2009. All of these applications are incorporated herein by reference.

STATEMENT REGARDING FEDERALLY SPONSORED RESEARCH

This invention was made with government support under Grant No. R01 HL57354, awarded by the National Institutes of Health. The government has certain rights in the invention.

SEQUENCE LISTING

A sequence accompanies this application and is attached as an Appendix. The sequence is incorporated herein by reference in its entirety.

BACKGROUND

With 55% of Americans overweight or obese, obesity and other associated metabolic diseases form the essence of a public health crisis in the United States. The role of physical activity in reducing the risk of obesity-associated diseases, such as cardiovascular disease and type 2 diabetes, is well-established. As more than half of U.S. adults are not meeting exercise recommendations, there appear to be behavioral barriers to maintaining a regular exercise program and thereby maximizing the health benefits of exercise. Furthermore, it is clear that not everyone accrues the same benefits in response to the same exercise exposure. It would be beneficial to identify genetic variations indicative of the likelihood of adherence to and physiological response to exercise programs.

SUMMARY

In one aspect, methods of predicting a trait in a subject are provided herein. The methods include obtaining information about at least a portion of an acid ceramidase polynucleotide sequence of the subject and then using the information to predict the expression of the trait in the subject. Obtaining information may include at least one of sequencing, RFLP analysis, amplification, primer extension, and microarray analysis. In another aspect, the methods include determining the sequence of a polynucleotide of the subject, the polynucleotide sequence encoding the acid ceramidase polypeptide, and using the sequence to predict the expression of the trait in the subject. In another aspect, the methods include analyzing the sequence of a polynucleotide of the subject, the polynucleotide sequence encoding the acid ceramidase polypeptide, and using the sequence to predict the expression of the trait in the subject. In another aspect, the methods include performing an assay to determine the sequence of a polynucleotide of the subject, the polynucleotide sequence encoding the acid ceramidase polypeptide, and using the sequence to predict the expression of the trait in the subject. In another aspect, the methods include detecting a nucleotide at a base position of the sequence of a polynucleotide of the subject, the polynucleotide sequence encoding the acid ceramidase polypeptide, and using the sequence to predict the expression of the trait in the subject.

In another aspect, methods of developing a treatment plan for a subject with a disease or condition responsive to exercise are provided. The methods include obtaining information about at least a portion of an acid ceramidase polynucleotide sequence of the subject. The information is then used to predict the expression of a trait selected from maintaining an exercise program and physiological responsiveness to an exercise program in the subject. In another aspect, the methods include determining the sequence of a polynucleotide of the subject, the polynucleotide sequence encoding the acid ceramidase polypeptide, and using the sequence to predict the expression of the trait in the subject selected from maintaining an exercise program and physiological responsiveness to an exercise program in the subject. In another aspect, the methods include analyzing the sequence of a polynucleotide of the subject, the polynucleotide sequence encoding the acid ceramidase polypeptide, and using the sequence to predict the expression of the trait in the subject selected from maintaining an exercise program and physiological responsiveness to an exercise program in the subject. In another aspect, the methods include performing an assay to determine the sequence of a polynucleotide of the subject, the polynucleotide sequence encoding the acid ceramidase polypeptide, and using the sequence to predict the expression of the trait in the subject selected from maintaining an exercise program and physiological responsiveness to an exercise program in the subject. In another aspect, the methods include detecting a nucleotide at a base position of the sequence of a polynucleotide of the subject, the polynucleotide sequence encoding the acid ceramidase polypeptide, and using the sequence to predict the expression of the trait in the subject selected from maintaining an exercise program and physiological responsiveness to an exercise program in the subject. A treatment plan can be developed for the subject to treat the disease or condition responsive to exercise.

In yet another aspect, methods of determining a nucleotide in a subject at a position in which a single polynucleotide polymorphism is correlated with a trait are provided. The methods include detecting a target polynucleotide in a sample with at least one oligonucleotide capable of binding to the target polynucleotide. The target polynucleotide comprises a nucleotide at a base position of acid ceramidase selected from the group consisting of rs2898458, rs7508, and rs3810. Then the nucleotide at the single nucleotide polymorphism in the subject is determined.

In still another aspect, kits comprising a first oligonucleotide capable of binding to a target polynucleotide are provided. In the kits the target polynucleotide comprises a nucleotide at a position of the acid ceramidase polynucleotide selected from the group consisting of rs2898458, rs7508, and rs3810. The kits may also include instructions for determining the nucleotide at the position in a sample from a subject.

DETAILED DESCRIPTION

Figure 1:
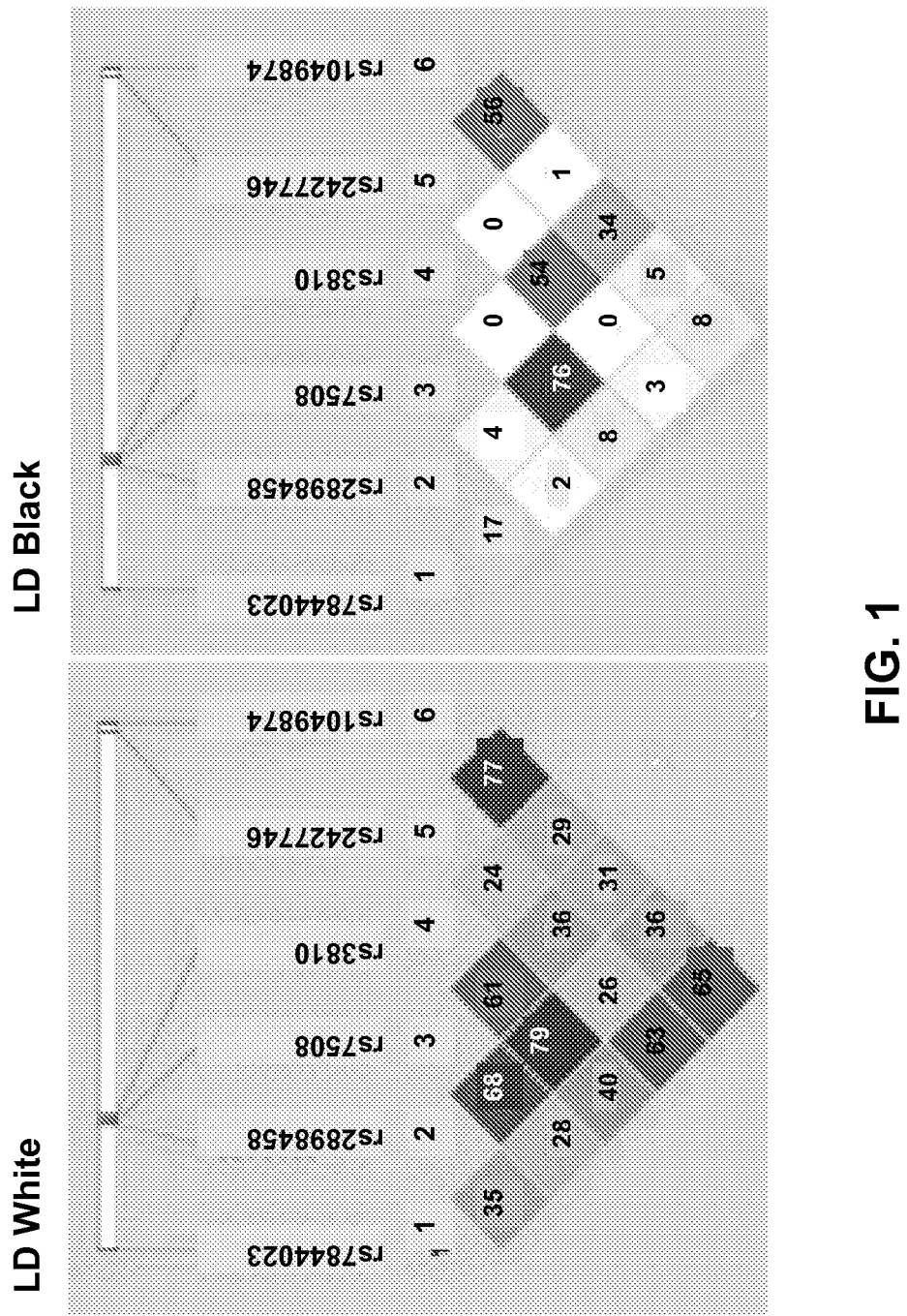
FIG. 1 are linkage disequilibrium plots for acid ceramidase SNPs.

Ceramide is a central compound in sphingolipid metabolism and mediates many biological processes related to stress responses including apoptosis, differentiation, and inflammation. Further, ceramide is important in metabolic signaling. It antagonizes insulin signaling and mitochondrial function and has been implicated in the apoptosis of pancreatic beta cells leading to type 2 diabetes and lipotoxic heart disease in obese rats. Further, the content of ceramide in cardiac and skeletal muscle is modulated by exercise training.

Despite the importance of ceramide in energy metabolism and the association of decreased tissue ceramide content to acquisition of a more favorable insulin signaling profile with exercise, the role of the main enzyme of ceramide metabolism, acid ceramidase (ASAH), is understudied. The role of acid ceramidase gene variants in exercise responses is unknown. In the Examples, acid ceramidase gene variants are shown to impact ceramide metabolism and other downstream metabolic responses to exercise, exercise capacity, and thereby exercise program maintenance. The Studies of Targeted Risk Reduction Interventions through Defined Exercise (STRRIDE), a randomized, controlled clinical trial, and the follow-up STRRIDE II study through which we are investigating the health benefits of exercise training in overweight and obese middle-aged inactive men and women formed the basis for the studies provided in the Examples. The association of single nucleotide polymorphisms (SNPs) in the acid ceramidase gene of the subject were shown to affect maintenance of exercise training and potential physiologic mediators thereof during a structured exercise intervention.

A method of predicting a trait in a subject is provided. The method includes obtaining information about a polynucleotide sequence encoding acid ceramidase of the subject. The information is predictive of the trait. As described in the Examples, single nucleotide polymorphisms may be detected within polynucleotide sequences encoding the acid ceramidase polypeptide of subjects. It was discovered that some of these polymorphisms are predictive of the likelihood of the individual maintaining an exercise program and the individual's physiological response to exercise, such as the improvement in the individual's peak oxygen consumption over time during an exercise program.

The information obtained about the polynucleotide sequence generally includes the identity of at least one nucleotide present at a particular position within the genome of the individual where a single nucleotide polymorphism (SNP) is identified. Polymorphisms are allelic variants that occur in a population that can be a single nucleotide difference present at a locus, or can be an insertion or deletion of one, a few or many consecutive nucleotides. A SNP is characterized by the presence in a population of two, three or four nucleotides (i.e., adenosine, cytosine, guanosine or thymidine) or an insertion or deletion of at least one nucleotide at a particular locus in genomes from different individuals. Typically less than all four nucleotides will occur at a single SNP site.

Several SNPs are described below and in the Examples. The Examples below demonstrate that the presence of a particular nucleotide in a specific identified SNP position is linked to the expression of a trait, such as maintaining an exercise program, in the individual. Thus the identity of the nucleotide(s) present in the subject at the SNP site may be indicative of subjects with a particular phenotype related to a trait. The identity of the nucleotide(s) present at the SNP in an individual may be used to predict whether the individual is likely to have a trait or express a particular phenotype related to the trait as compared to other individuals. Predicting and prediction as used herein includes, but is not limited to, generating a statistically based indication of whether a particular subject will have a particular trait or express a particular phenotype. Predicting may also include using the statistical information found in the Examples or generated by another entity to generate predictions about a subject. Alternatively, predicting may include any means available to use the information obtained to assess an individual's likelihood of expressing the trait or phenotype. This does not mean that the trait or phenotype will occur with 100% certainty.

A polynucleotide and amino acid sequence of acid ceramidase is provided in the attached Appendix (Gene ID 427; ASAH1—SEQ ID NO:1 and SEQ ID NO:2, respectively). Several SNPs are identified in the Examples and are shown to be correlated with adherence to an exercise program and also to physiologic responses of the individual over the course of an exercise program, such as the rate of improvement in peak oxygen consumption. The SNPs identified as related to these traits are rs2898458, rs7508, and rs3810. In particular, the presence of an adenine at rs2898458, an adenine at rs7508, or a guanine at rs3810 is associated with increased likelihood of adherence to an exercise program and increased rate of and overall improved physiologic response to an exercise program over time. Alternatively, the presence of a guanine at rs2898458, a guanine at rs7508, or a thymine at rs3810 is associated with decreased likelihood of maintaining an exercise program and decreased rate of and overall poor improvement in physiologic response to an exercise program over time. Other SNPs in the acid ceramidase sequence may also correlate to the traits described herein. Additionally, the presence of the identified SNPs may be predictive or indicative of additional traits or phenotypes in individuals.

The information about the polynucleotide sequence may be obtained by any method, including those known to those of skill in the art. For example, the information may be obtained by sequencing, restriction fragment length polymorphism (RFLP) analysis, differential amplification, primer extension, or microarray analysis. Alternatively, the information can be obtained from a separate entity, such as an independent testing laboratory. In the Examples, the polynucleotides from individual subjects were amplified using polymerase chain reaction.

Some of the polymorphisms may result in an amino acid change in the polypeptide encoded by the polynucleotide. These single nucleotide polymorphisms can be detected and information about the polynucleotide obtained by any method capable of detecting amino acid changes in a polypeptide, e.g., using protease digestion or Western blot analysis using antibodies specific to an epitope encompassing the amino acid change.

A trait is a characteristic of an organism that manifests itself in a phenotype. Many traits are the result of the expression of a single gene, but some are polygenic (i.e., result from simultaneous expression of more than one gene). A phenotype is an outward appearance or other visible characteristic of an organism. In the Examples, likelihood of an individual to maintain an exercise program and to improve the peak oxygen consumption during exercise program participation was predicted.

The information used to predict the occurrence of the trait or the phenotype in an individual subject may be analyzed by any means available to those skilled in the art. Comparing the test subject to a number of subjects with a known nucleotide at the SNP site and a known phenotype of the trait allows prediction of the trait or phenotype in the test subject. Those skilled in the art will appreciate that statistical methods, such as those described in the Examples, may be used to make predictions. Relationships between nucleotide occurrences of one or more SNPs and a trait can be identified using known statistical methods. A statistical analysis result which shows an association of one or more SNPs with a trait with at least 70%, 75%, 80%, 85%, 90%, 95%, 98%, or 99% confidence, or alternatively a probability of insignificance less than 0.10, less than 0.05, or less than 0.01, can be used to identify SNPs associated with a trait. These statistical tools may test for significance related to a null hypothesis that a SNP is not significantly different between groups with different traits. If the significance of this difference is low, it suggests the allele is not related to a trait.

In diploid organisms such as humans, somatic cells include two alleles for each locus. The two alleles are referred to herein as a genotype or as a diploid pair, and the analysis of somatic cells, typically identifies the alleles for each copy of the gene. The methods provided herein include identifying a diploid pair of alleles. These alleles can be identical (homozygous) or can be different (heterozygous).

A sample useful for practicing the methods described herein can be any biological sample of a subject, typically a human subject. The sample contains nucleic acid molecules, including portions of the gene sequences to be examined, or corresponding encoded polypeptides, depending on the particular method used. The sample can be a cell, tissue, or organ sample, or can be a sample of a biological material such as a body fluid, for example blood or saliva. A nucleic acid sample useful for practicing the methods provided herein may be DNA or RNA. The nucleic acid sample generally is a DNA sample, suitably genomic DNA. A cDNA sample or amplification product thereof can also be used. Where the SNPs are present in a coding region of a gene, the nucleic acid sample can be DNA or RNA, or products derived therefrom. Particular SNPs may be in coding regions of a gene and can result in polypeptides containing different amino acids at the positions corresponding to the SNPs due to a change to a codon encoding a distinct amino acid. The methods described herein can also be practiced using a sample containing polypeptides of the subject.

Any suitable method may be used to determine the nucleotide occurrence for a particular SNP in a sample, including any of numerous methods available to those of skill in the art. Such methods can utilize one or more oligonucleotide probes or primers, including, for example, an amplification primer pair that selectively hybridizes to a target polynucleotide that includes one or more of the associated bovine SNPs. Oligonucleotide probes useful in practicing the methods can include, for example, an oligonucleotide that is complementary to a portion of the target polynucleotide, including the position of the SNP, wherein the presence of a specific nucleotide at the position (i.e., the SNP) is detected by the presence or absence of selective hybridization of the probe. Such a method can include contacting the target polynucleotide and hybridized oligonucleotide with an endonuclease, and detecting the presence or absence of a cleavage product of the probe, depending on whether the nucleotide occurrence at the SNP site is complementary to the corresponding nucleotide of the probe.

An oligonucleotide ligation assay may be used to identify a nucleotide occurrence at a polymorphic position. In this assay a pair of probes that selectively hybridize upstream and adjacent to and downstream and adjacent to the site of the SNP are used. One of the probes includes a terminal nucleotide (3'-nucleotide) complementary to a nucleotide occurrence of the SNP. Where the terminal nucleotide of the probe is complementary to the nucleotide occurrence, selective hybridization includes the terminal nucleotide such that, in the presence of a ligase, the upstream and downstream oligonucleotides are ligated. The presence or absence of a ligation product is indicative of the nucleotide occurrence at the SNP site.

An oligonucleotide also can be useful as a primer, for example, for a primer extension reaction, wherein the product (or absence of a product) of the extension reaction is indicative of the nucleotide occurrence. In addition, a primer pair useful for amplifying (i.e. by PCR) a portion of the target polynucleotide including the SNP site can be useful. In this assay, the amplification product is examined to determine the nucleotide occurrence at the SNP site. Particularly useful methods include those that are readily adaptable to a high throughput format, to a multiplex format, or to both. The primer extension or amplification product can be detected directly or indirectly and/or can be sequenced using various methods known in the art. Amplification products which span a SNP locus can be sequenced using traditional sequence methodologies. Alternatively, the products may be analyzed by RFLP analysis by treating the amplification products with restriction endonucleases which will differentially digest the products based on the nucleotide present at the SNP site.

Methods of the invention can identify nucleotide occurrences at SNPs using genome-wide sequencing or "microsequencing" methods. Whole-genome sequencing of individuals identifies all SNP genotypes in a single analysis. Microsequencing methods determine the identity of only a single nucleotide at a "predetermined" site. Such methods have particular utility in determining the presence and identity of SNPs in a target polynucleotide. Such microsequencing methods, as well as other methods for determining the nucleotide occurrence at a SNP locus are available to those skilled in the art.

The nucleotide present at a SNP can also be identified using an immunoassay specific for one or more of the nucleotides at the SNP site. The SNP can also be identified by contacting polynucleotides in the sample or polynucleotides derived from the sample, with a specific binding pair member that selectively hybridizes to a polynucleotide region comprising the SNP, under conditions wherein the binding pair member specifically binds at or near the SNP. The specific binding pair member can be an antibody or a complementary polynucleotide.

The nucleotide present at a SNP can be identified by other methods as well as those discussed above. For example, sequencing methods such as mass spectrometry, scanning electron microscopy, or methods in which a polynucleotide flows past a sorting device that can detect the sequence of the polynucleotide. The occurrence of a SNP can be identified using electrochemical detection devices as well. Other formats include melting curve analysis using fluorescently labeled hybridization probes, or intercalating dyes.

The methods of identifying the nucleotide present at a SNP may also utilize selective hybridization such as a microarray. Selective hybridization refers to hybridization under moderately stringent or highly stringent conditions such that a nucleotide sequence preferentially associates with a selected nucleotide sequence over unrelated nucleotide sequences to a large enough extent to be useful in identifying a nucleotide occurrence at a SNP. The nucleotide may be detected by comparing the amount of labeled oligonucleotide that binds to target nucleic acid molecule as compared to a nucleic acid molecule other than the target molecule, particularly a substantially similar (i.e., homologous) nucleic acid molecule other than the target nucleic acid molecule. Conditions that allow for selective hybridization can be determined empirically, or can be estimated based, for example, on the relative GC:AT content of the hybridizing oligonucleotide and the sequence to which it is to hybridize, the length of the hybridizing oligonucleotide, and the number of mismatches between the oligonucleotide and sequence to which it is to hybridize.

Methods of determining a nucleotide at a position that is correlated with expression of a trait in a sample are also provided. The method includes detecting a target polynucleotide in a sample using at least one oligonucleotide capable of binding to the target polynucleotide. The target polynucleotide includes a nucleotide at a position of acid ceramidase selected from the group consisting of rs2898458, rs7508, and rs3810. The identification of the nucleotide present at the SNP position in the subject is determined. The identification of the nucleotide may be determined by analyzing the binding of the oligonucleotide to the target polynucleotide. Alternatively, the nucleotide may be determined by a variety of other means, including but not limited to, differential amplification, restriction fragment length polymorphism, DNA sequencing, primer extension, or DNA ligation as described above.

Kits for determining the nucleotide present at a particular position within a subject are also provided. The kits may be used to perform the methods described herein. The kits include a first oligonucleotide capable of binding to a target polynucleotide. The oligonucleotide may be used as a probe, primer, or combined with a second oligonucleotide capable of binding the complement to the target polynucleotide to amplify the target polynucleotide. The target polynucleotide comprises a nucleotide at a position of acid ceramidase selected from the group consisting of rs2898458, rs7508, and rs3810. The target polynucleotides correspond to a portion of an acid ceramidase gene of SEQ ID NO:1 containing one or more SNP with a nucleotide associated with a trait in a subject. In addition, the kits may contain reagents for performing methods described herein including, but not limited to, one or more detectable labels, which can be used to label a probe or primer or can be incorporated into a product generated using the probe or primer (e.g., an amplification product); one or more polymerases, which can be useful for a method that includes a primer extension or amplification procedure; or other enzyme or enzymes (e.g., a ligase or an endonuclease), which can be useful for performing an oligonucleotide ligation assay or a mismatch endonuclease cleavage assay; and/or one or more buffers or other reagents that are necessary to or can facilitate performing the methods. The primers or probes can be included in a kit in a labeled form, for example with a label such as biotin or an antibody. The kits may also include instructions for performing the method or for analyzing the results and making predictions based on the results.

Also provided are methods of developing a treatment plan for a subject with a disease or condition responsive to exercise. The method includes obtaining information about at least a portion of an acid ceramidase polynucleotide sequence of the subject. The information is then used to predict a trait in the subject. The trait can include the likelihood of the subject to maintain an exercise program or the likelihood and quality of the subject's physiological response to an exercise program. The prediction is then used to develop an appropriate treatment plan for the subject to treat the disease or condition. Diseases and conditions responsive to exercise include, but are not limited to, overweight and obesity, cardiovascular disease, diabetes mellitus, stroke, osteoporosis, and cancer. The treatment plan may include monitoring, direct supervision of exercise, use of personal trainers or other aids to induce compliance with exercise, or increased pharmaceutical intervention to compensate for lack of exercise effectiveness in individuals less likely to maintain an exercise program or less likely to respond to exercise physiologically.

The Examples illustrate the various embodiments of the invention, but do not limit the scope of the attached claims.

EXAMPLES

Example 1

Methods

Subjects.

A complete description of the STRRIDE study design is published elsewhere (Kraus W E, et al. *Medicine and Science in Sports and Exercise* 2001 33: 1774-1784, incorporated herein by reference in its entirety). In summary, subjects were 40 to 65 years of age, sedentary (exercised less than once weekly), overweight or obese (BMI 25 to 35 kg/m$^2$), and had fasting hyperinsulinemia (>10 IU/mL) with mild to moderate lipid abnormalities (LDL cholesterol between 130 and 190 mg/dL or HDL cholesterol <45 mg/dL for women or <40 mg/dL for men). In STRRIDE II, subjects were 18 to 70 years of age, similarly overweight or obese, and sedentary with mild lipid abnormalities. In STRRIDE 1380 study subjects and in STRRIDE II 249 subjects met inclusion criteria and were randomized to one of four exercise groups in each study after providing informed consent as approved by the Investigational Review Boards of Duke and East Carolina University.

Exercise Training.

In the STRRIDE I study, subjects were randomly assigned to one of four groups: (1) non exercising control, (2) low volume/moderate intensity aerobic exercise, defined as a caloric equivalent of 12 miles/week at 40-55% peak oxygen consumption (peak VO$_2$), (3) low volume/vigorous intensity, defined as the caloric equivalent of 12 miles/week at 65-80% peak VO$_2$, and (4) high volume/vigorous intensity exercise, defined as the caloric equivalent of 20 miles/week at 65-85% peak VO$_2$. Caloric equivalents were determined by the approximate energy expenditure during walking or jogging for a 90 kg person, however actual exercise modalities included cycle ergometers, treadmills, and elliptical trainers. The subjects underwent a two month ramp period in which exercise intensity and duration were gradually increased until the appropriate regimen was reached, followed by an additional six months of exercise training In the STRRIDE II study, subjects underwent a three month control run-in period followed by an eight month exercise intervention in one of four exercise groups: (1) moderate amount aerobic training, identical to the low amount/vigorous intensity group of STRRIDE I (12 miles/week at 65-80% peak VO$_2$), (2) resistance training, in which subjects complete a regimen consisting of three sessions per week in which nine resistance exercises were performed at 70 to 85% of one repetition maximum weight, (3) moderate aerobic training plus resistance training, in which subjects completed the low volume/vigorous intensity aerobic training protocol in addition to the resistance training protocol, and (4) high volume/vigorous intensity aerobic training, identical to the high amount/vigorous intensity group of STRRIDE I (20 miles/week at 65-85% peak VO$_2$).

Biologic Measures.

All phenotypic measures were taken prior to initiation of exercise protocol and at completion of exercise intervention (Month 6 in STRRIDE I and Month 8 in STRRIDE II).

Genotyping.

DNA was isolated from whole blood using a commercial DNA isolation kit and a standard protocol (Qiagen Inc, Valencia, Calif.). Acid ceramidase (ASAH) SNPs were identified using the SNPSelector program in which a tagging algorithm prioritized SNPs for linkage disequilibrium, allelic frequencies, and regulatory potential (Xu H, et al. *Bioinformatics* 2005 21: 4181-4186, incorporated herein by reference in its entirety). Six haplotype tagging SNPs in the ASAH gene were identified: rs7844023, rs2898458, rs7508, rs3810, rs2427746, and rs1049874. These SNPs were genotyped using the Taqman assay (Applied Biosystems, Foster City, Calif.). The Taqman genotyping reaction was then amplified using a GeneAmp PCR system 9700 (95° C. for 10 min, then 50 cycles at 92° C. for 15 sec, 60° C. for 1 min) with the primers shown in Table 1 (SEQ ID NOs: 3-5). Fluorescence was detected using the 7900HT Taqman sequence detector (Applied Biosystems). Two reference controls were included. All SNPs examined were successfully genotyped for 95% or more of the individuals in the study, and rescreening of 2.4% of subjects gave 100% identical results. Error rate estimates for SNPs meeting the reference control benchmarks were <0.2%.

group, genotype by race, and genotype by gender) and when significant at the p<0.1 level were retained in the model. For all drop-out and percent compliance analyses, the STRRIDE II study participants were analyzed primarily with the STRRIDE I dataset used as a validation analysis.

Multivariate linear regression models were created to quantify genotypic effects on peak oxygen consumption (peak $VO_2$) while controlling for race, gender and exercise group effects both prior to initiation of the study and after completion of the exercise intervention, with improvement in biologic marker being the dependent variable. Initial models using only the STRRIDE I dataset did not reach significance, probably due to a lack of power. Therefore, for all baseline and change biologic measures models, the STRRIDE I and STRRIDE II datasets were combined to increase power. Data are presented as mean±SE. Haploview was used to assess linkage disequilibrium (LD) between SNPs (Barrett J C, et al. *Bioinformatics* 2005 21: 263-265, incorporated herein by reference in its entirety) using the combined STRRIDE I and STRRIDE II datasets.

TABLE 1

Primer Sequences

| Oligonucleotide | Strand | Reference |
|---|---|---|
| GTCATGTAAGAGTAAGATTGTGACC[A/G]TTTAGTCATATTTAATAACCCACTT | Forward | rs2898458 SEQ ID NO: 3 |
| TGACTGCTGACTGGCACTCTTTCCA[A/G]TGACTGTTTATTGAGTGTCAGGAAC | Forward | rs7508 SEQ ID NO: 4 |
| CTATTAGTACTTTTCATAAGCAGTT[G/T]GATTTCTGAAAAATACAGTAACATA | Reverse | rs3810 SEQ ID NO: 5 |

Statistical Analysis.

Data were analyzed using logistic regression and analysis of variance models (SAS software, SAS Institute, Cary, N.C.). Program completion was measured as a dichotomous variable (completion of study versus drop-out from study) and exercise compliance as a percentage of total prescribed exercise completed for those finishing the study. Genotype analyses were performed both as a continuous allelic variable and also as a dominant allelic variable (presence versus absence of minor allele, regardless of copy number). Logistic regression models were used to quantify genotype effects on risk of drop-out from study. To control for multiple comparisons, main effects for any given SNP were considered significant at p<0.01. Data are presented as odds ratios. Multivariate linear regression was used to model genotype effect on percent compliance. All models controlled for gender, race, and exercise group effects. Interactions were tested (genotype by Example 2

Results

Allele Frequencies.

Six ASAH SNPs were genotyped (rs7844023, rs2898458, rs7508, rs3810, rs2427746, rs1049874) in 239 subjects in STRRIDE I and 246 subjects in STRRIDE II. All allele frequencies (Table 2) were in Hardy Weinberg equilibrium ($chi^2$ test, P>0.05) except for rs1049874. Shown in FIG. 1 are linkage disequilibrium plots for genotype in white subjects (left) and black subjects (right) participating in either STRRIDE I or STRRIDE II. Results given are $r^2$ values for association. Three SNPs, rs2898458, rs7508, and rs3810, were in pairwise LD in whites (n=371). SNPs rs2427746 and rs1049874 were in strong LD in whites (n=371). Only SNPs rs2898458 and rs3810 were in strong LD in blacks (n=114).

TABLE 2

| | | Allele Frequencies by Minor Allele | | | | | |
|---|---|---|---|---|---|---|---|
| | | Homozygous Major Allele | | Heterozygous | | Homozygous Minor Allele | |
| | | STRRIDE 1 | STRRIDE II | STRRIDE 1 | STRRIDE II | STRRIDE 1 | STRRIDE II |
| rs7844023 | White | 26.47 | 24.47 | 46.47 | 53.19 | 27.06 | 22.34 |
| (C > T) | Black | 25.86 | 30.77 | 46.55 | 40.38 | 27.59 | 28.85 |

TABLE 2-continued

Allele Frequencies by Minor Allele

| | | Homozygous Major Allele | | Heterozygous | | Homozygous Minor Allele | |
|---|---|---|---|---|---|---|---|
| | | STRRIDE 1 | STRRIDE II | STRRIDE 1 | STRRIDE II | STRRIDE 1 | STRRIDE II |
| rs2898458 | White | 50.3 | 44.44 | 38.18 | 47.62 | 11.52 | 7.94 |
| (A > G) | Black | 7.41 | 22 | 40.74 | 38 | 51.85 | 40 |
| rs7508 | White | 59.41 | 53.68 | 32.94 | 40.53 | 7.65 | 5.79 |
| (A > G) | Black | 81.03 | 90.38 | 13.79 | 9.62 | 5.17 | 0 |
| rs3810 | White | 45.29 | 43.09 | 41.76 | 48.4 | 12.94 | 8.51 |
| (G > T) | Black | 7.14 | 11.76 | 39.29 | 45.1 | 53.57 | 41.14 |
| rs2427746 | White | 35.5 | 27.51 | 41.42 | 49.74 | 23.08 | 22.75 |
| (A > G) | Black | 62.96 | 70.59 | 29.63 | 27.45 | 7.41 | 1.96 |
| rs1049874 | White | 34.32 | 22.99 | 36.69 | 51.34 | 28.99 | 25.67 |
| (T > C) | Black | 56.9 | 54.9 | 31.03 | 37.25 | 12.07 | 7.84 |

Genetic Effects on Odds of Drop Out from Study and Exercise Compliance.

Figure 2:
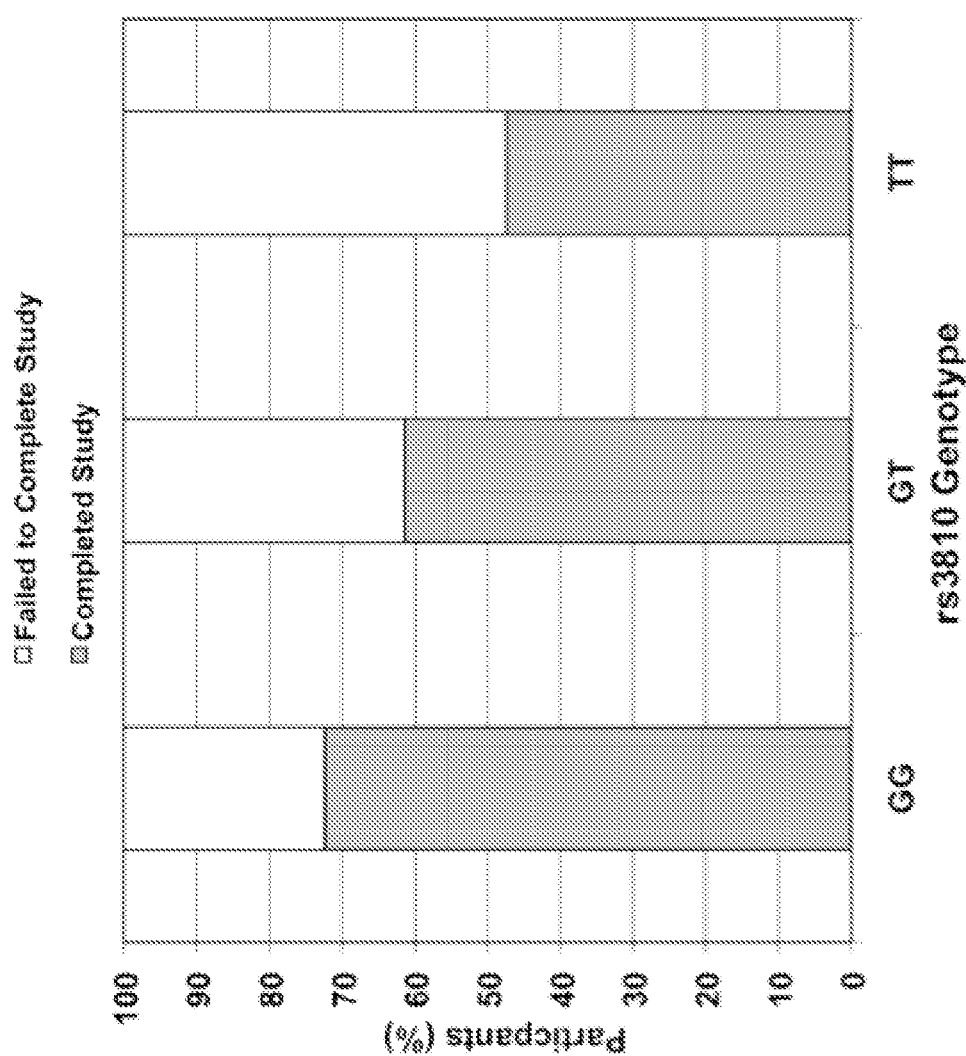
FIG. 2 is a graph of the percent of participants in each group with each genotype at SNP rs3810.
Figure 3:
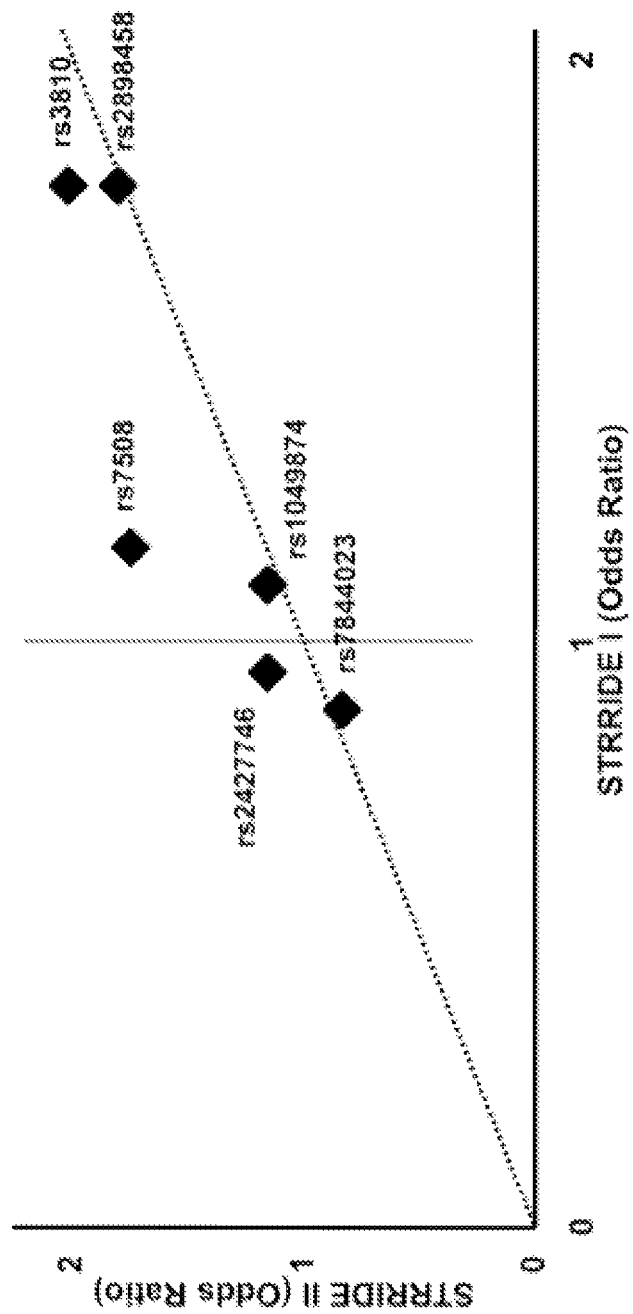
FIG. 3 is a graph of the odds ratios for risk of drop-out for each SNP in STRRIDE I compared to STRRIDE II.

Table 3 shows the odds ratio estimates and significance values for the effect of each SNP on the probability of drop-out from both STRRIDE I and STRRIDE II studies. Three ASAH SNPs, rs2898458, rs7508, and rs3810 consistently predicted drop-out. These are the same SNPs shown to be in LD in our dataset as discussed above. In STRRIDE II, the SNPs were significantly associated with drop out in both allelic and dominant models. For example, as shown in FIG. 2, in the allelic model for SNP rs3810 each additional minor allele carried by a subject doubled the odds of drop-out from STRRIDE II when controlled for group, gender, and race. Shown in FIG. 2 are the percent of subjects in STRRIDE II completing the exercise intervention compared to rs3810 genotype (GG n=87; GT n=114; TT n=38). In the dominant model, subjects with either one or two copies of the minor allele were almost 3.5 times more likely to drop out than those with the homozygous dominant genotype. Both models for rs3810 were significant (p=0.012 for the allelic model and p=0.0053 in the dominant model). The results for rs3810 were validated in the STRRIDE I dataset, in which the allelic model significantly predicted drop out (OR=1.79, p=0.0164). Similarly in STRRIDE II, both rs2898458 and rs7508 significantly increased the odds of drop out in both the allelic and dominant models. In the validation dataset, rs2898458 was found to again significantly predict drop out in the allelic model. Regardless of significance, the direction and magnitude of effect of each SNP on drop out in STRRIDE II was replicated in STRRIDE I (FIG. 3). Shown in FIG. 3 are odds ratios for risk of drop-out for each SNP in STRRIDE I compared to STRRIDE II in the allelic genotype model. For all SNPs except rs2427746 the direction of effect is the same in both studies. Having two SNPs significantly increased the odds of drop-out in both STRRIDE II and STRRIDE I: rs2898458 and rs3810. SNP rs7508 significantly increased the odds of drop out in STRRIDE II.

TABLE 3

Genotype Effect on Risk of Drop-Out from Study

| | | Allelic Model | | Dominant Model | |
|---|---|---|---|---|---|
| | | OR | P Value | OR | P Value |
| rs7844023 | STRRIDE I | 0.88 | 0.562 | 0.88 | 0.3 |
| | STRRIDE II | 0.86 | 0.513 | 0.82 | 0.596 |

TABLE 3-continued

Genotype Effect on Risk of Drop-Out from Study

| | | Allelic Model | | Dominant Model | |
|---|---|---|---|---|---|
| | | OR | P Value | OR | P Value |
| rs2898458 | STRRIDE I | 1.8 | 0.022 | 1.8 | 0.384 |
| | STRRIDE II | 1.79 | 0.026 | 2.52 | 0.018 |
| rs7508 | STRRIDE I | 1.17 | 0.546 | 1.17 | 0.499 |
| | STRRIDE II | 1.78 | 0.002 | 2.55 | 0.015 |
| rs3810 | STR.RIDE I | 1.79 | 0.016 | 1.79 | 0.687 |
| | STRRIDEII | 2.02 | 0.012 | 3.49 | 0.005 |
| rs2427746 | STRRIDE I | 0.95 | 0.838 | 0.95 | 0.455 |
| | STRRIDE II | 1.17 | 0.656 | 1.15 | 0.711 |
| rs1049874 | STRRIDE I | 1.11 | 0.635 | 1.11 | 0.92 |
| | STRRIDE II | 1.18 | 0.628 | 1.21 | 0.628 |

In the allelic model for rs7508, two interaction terms reached significance and were left in the model. There was an interaction between genotype effect and exercise group. When the model was stratified by group, the genotype effect remained significant in the aerobic plus resistance training group (p=0.0377). Within this group, each additional minor allele increased the odds of drop out five times. Interestingly, when the allelic model for rs7508 was stratified by gender, the genotype effect was significant in males only (p=0.01) in which the odds ratio for drop out per minor allele was 4.3. Compliance as a percentage of total exercise prescription completion was also tested for genotypic association in those finishing the exercise program. These correlations did not reach significance likely due to the lack of end-point data for the non-completers.

Genetic Effects on Peak Oxygen Consumption.

Figure 4:
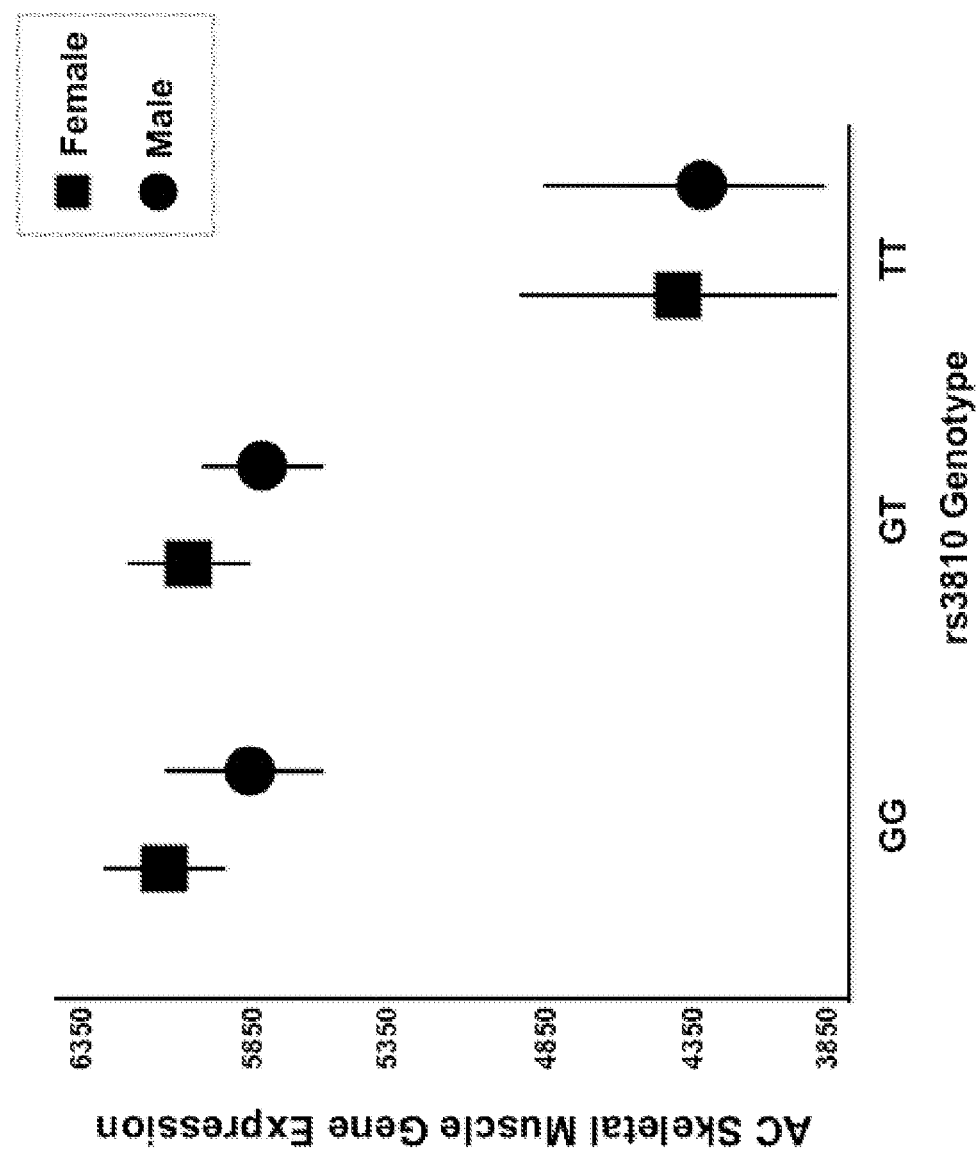
FIG. 4 is a graph showing the improvement in peak oxygen consumption (peak $VO_2$) with exercise by rs3810 genotype.

To investigate potential mediators of the gene effect findings on drop out and adherence we studied the effects of the same ASAH gene variants on baseline peak $VO_2$ and change in peak $VO_2$ with exercise training, hypothesizing that poor exercise capacity or ability to respond to exercise training might affect exercise compliance. Baseline measurements of peak $VO_2$ prior to exercise intervention were not significantly associated with genotype or rate of compliance with exercise. In subjects who completed the exercise study, improvement in peak $VO_2$ was correlated with genotype in two of the three ASAH SNPs discussed above. Most significantly, in the allelic model of SNP rs3810, each additional minor allele decreased the improvement in peak oxygen consumption by 1.4 (mL/kg/min) when compared to subjects homozygous for the major allele and controlling for race, gender, group, and baseline peak $VO_2$ (p=0.0185, $r^2$=0.3689). This is shown in FIG. 4, wherein actual improvement in peak $VO_2$ (mL/kg/ min), measured as the difference in peak VO$_2$ before and after an exercise intervention, was compared to rs3810 genotype. STRRIDE I and STRRIDE II datasets were combined for the analysis (GG genotype n=168, GT genotype n=207, TT genotype n=90). The rs3810 genotype significantly predicted change in peak VO$_2$ (p=0.0185). The minor allele of SNP rs2898458 was also correlated with a decreased improvement of peak VO$_2$ after exercise training. This allelic model trended towards significance (p=0.0734, r$^2$=0.362). Interestingly, improvement in peak oxygen consumption with exercise significantly predicted rate of compliance (p=0.047) when controlling for race, gender, and exercise group.

We claim:

1. A method of predicting a trait in a subject, the method comprising:
    obtaining a biological sample from the subject, wherein the subject is overweight or obese;
    identifying by polymerase chain reaction (PCR) a nucleotide at a base position of an acid ceramidase polynucleotide sequence in the biological sample, wherein the base position is selected from the group consisting of: rs2898458, rs7508, and rs3810, wherein the PCR is performed with a nucleic acid sequence selected from the group consisting of: SEQ ID NO:3, SEQ ID NO:4, and SEQ ID NO:5, and wherein the nucleic acid sequence is labeled with a fluorophore; and
    predicting the expression of the trait in the subject based upon the identity of the nucleotide.

2. The method of claim 1, wherein the trait is selected from the group consisting of maintenance of exercise program, physiologic response to an exercise program, and peak oxygen consumption improvement during an exercise program.

3. The method of claim 1, wherein the nucleotide at the base position (rs2898458) is identified and a guanine is predictive of a trait selected from at least one of low likelihood of adherence to an exercise program, reduced physiological response to an exercise program, and minimal improvement in peak oxygen consumption during an exercise program.

4. The method of claim 1, wherein the nucleotide at rs2898458 is identified and an adenine is predictive of a trait selected from at least one of increased likelihood of adherence to an exercise program, a positive physiological response to an exercise program, and improvement in peak oxygen consumption during an exercise program.

5. The method of claim 1, wherein the nucleotide at rs7508 is identified and a guanine is predictive of a trait selected from at least one of low likelihood of adherence to an exercise program, reduced physiological response to an exercise program, and minimal improvement in peak oxygen consumption during an exercise program.

6. The method of claim 1, wherein the nucleotide at rs7508 is identified and an adenine is predictive of a trait selected from at least one of increased likelihood of maintaining an exercise program, a positive physiological response to an exercise program, and improvement in peak oxygen consumption during an exercise program.

7. The method of claim 1, wherein the nucleotide at rs3810 is identified as a thymine and the thymine is predictive of a trait selected from at least one of low likelihood of maintaining an exercise program, reduced physiological response to an exercise program, and minimal improvement in peak oxygen consumption during an exercise program.

8. The method of claim 1, wherein the nucleotide at rs3810 is identified as a guanine and the guanine is predictive of a trait selected from at least one of increased likelihood of maintaining an exercise program, a positive physiological response to an exercise program, and improvement in peak oxygen consumption during an exercise program.

9. The method of claim 1, further comprising developing a treatment plan for the subject based upon the predicted expression of the trait in the subject,
  wherein the treatment plan includes supervision of exercise or pharmaceutical intervention when the nucleotide at rs3810 is identified as a thymine, the nucleotide at rs2898458 is identified as a guanine, or the nucleotide at rs7508 is identified as an guanine, and
  wherein the thymine at rs3810, the guanine at rs2898458, or the guanine at rs7508 is predictive of a trait selected from at least one of low likelihood of maintaining an exercise program, reduced physiological response to an exercise program, and minimal improvement in peak oxygen consumption during an exercise program.

* * * * *